United States Patent
Cuomo et al.

[11] Patent Number: 5,284,566
[45] Date of Patent: Feb. 8, 1994

[54] ELECTROCHEMICAL GAS SENSOR WITH WRAPAROUND REFERENCE ELECTRODE

[75] Inventors: Carlo E. Cuomo, Verona; Alfred Kutschker, Baden; Peter M. Noble, Valencia; Robert L. Novack, Evans, all of Pa.

[73] Assignee: Bacharach, Inc., Pittsburgh, Pa.

[21] Appl. No.: 182

[22] Filed: Jan. 4, 1993

[51] Int. Cl.$^5$ .................................... G01N 27/26
[52] U.S. Cl. .................... 204/412; 204/431; 204/432; 204/415
[58] Field of Search ............ 204/412, 415, 431, 432

[56] References Cited

U.S. PATENT DOCUMENTS

| | | | |
|---|---|---|---|
| Re. 31,914 | 6/1985 | Oswin et al. | 204/1 |
| Re. 31,915 | 6/1985 | Oswin et al. | 204/412 |
| Re. 31,916 | 6/1985 | Oswin et al. | 204/412 |
| 3,755,125 | 8/1973 | Shaw et al. | 204/195 |
| 3,950,980 | 4/1976 | Braun et al. | 73/23 |
| 4,025,412 | 5/1977 | LaConti | 204/195 |
| 4,132,616 | 1/1979 | Tantram et al. | 204/195 |
| 4,406,770 | 9/1983 | Chan et al. | 204/406 |
| 4,521,290 | 6/1985 | Venkatasetty | 204/412 |
| 4,587,003 | 5/1986 | Tantram et al. | 204/412 |
| 4,633,704 | 1/1987 | Tantram et al. | 73/23 |
| 4,769,122 | 9/1988 | Marrese et al. | 204/408 |
| 4,775,456 | 10/1988 | Shah et al. | 204/412 |
| 4,894,138 | 1/1990 | Gambert et al. | 204/415 |
| 4,948,496 | 8/1990 | Chand | 204/408 |
| 4,960,497 | 10/1990 | Gallagher, deceased | 204/153.16 |
| 4,961,834 | 10/1990 | Kuhn et al. | 204/412 |
| 4,988,429 | 1/1991 | Matthiessen | 204/408 |

FOREIGN PATENT DOCUMENTS 2140566 11/1984 United Kingdom ................ 27/28

Primary Examiner—John Niebling
Assistant Examiner—Bruce F. Bell
Attorney, Agent, or Firm—Webb, Burden, Ziesenheim & Webb

[57] ABSTRACT

An electrochemical sensor for detecting gas includes stacked reference, counter and sensing electrodes within a body and having a quantity of a liquid electrolyte in an electrolyte chamber therein. A support is provided for holding the electrodes and mats in contact with each other and at an inner end of a cavity within the sensor. A gas passage, such as a diffusion limiter, is provided through the sensor body and permits gas to reach the sensing electrode. The reference electrode is formed in a wraparound structure, with the reference electrode provided with a plurality of integral extensions which extend around the support and the counter electrode and into contact with the liquid electrolyte, thereby providing a large reference electrode fitted into a small body.

20 Claims, 4 Drawing Sheets

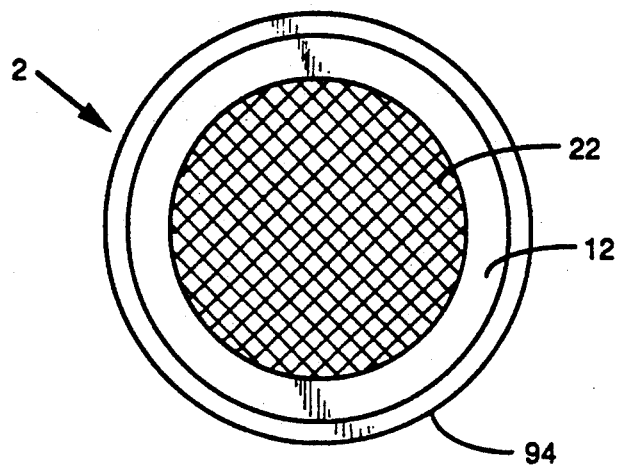
FIG. 1
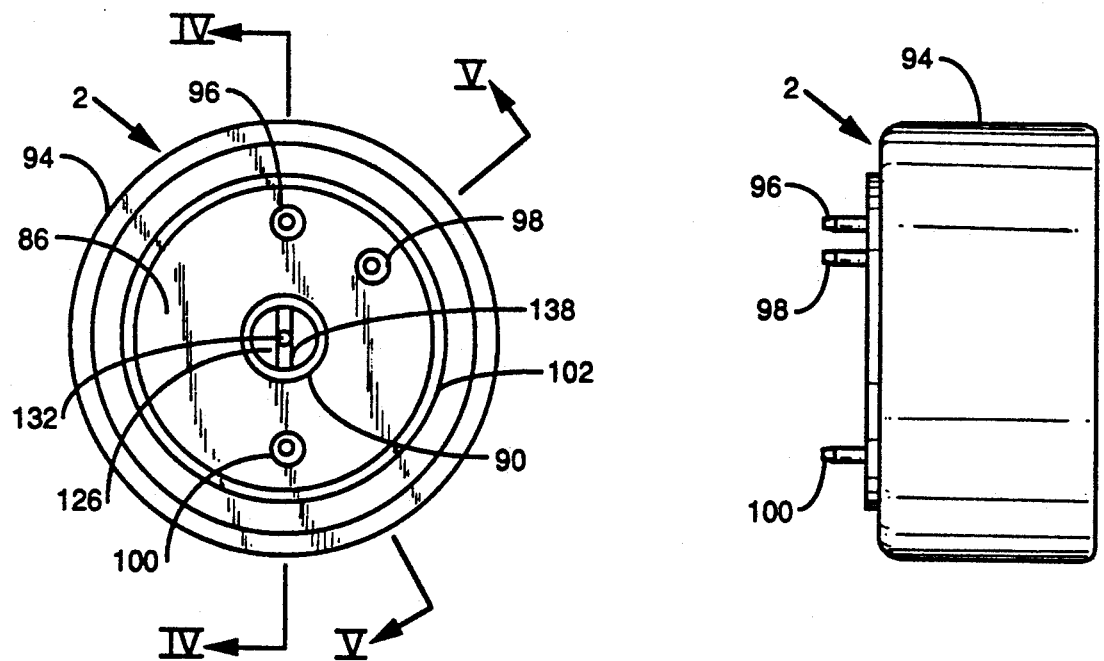
FIG. 2
FIG. 3

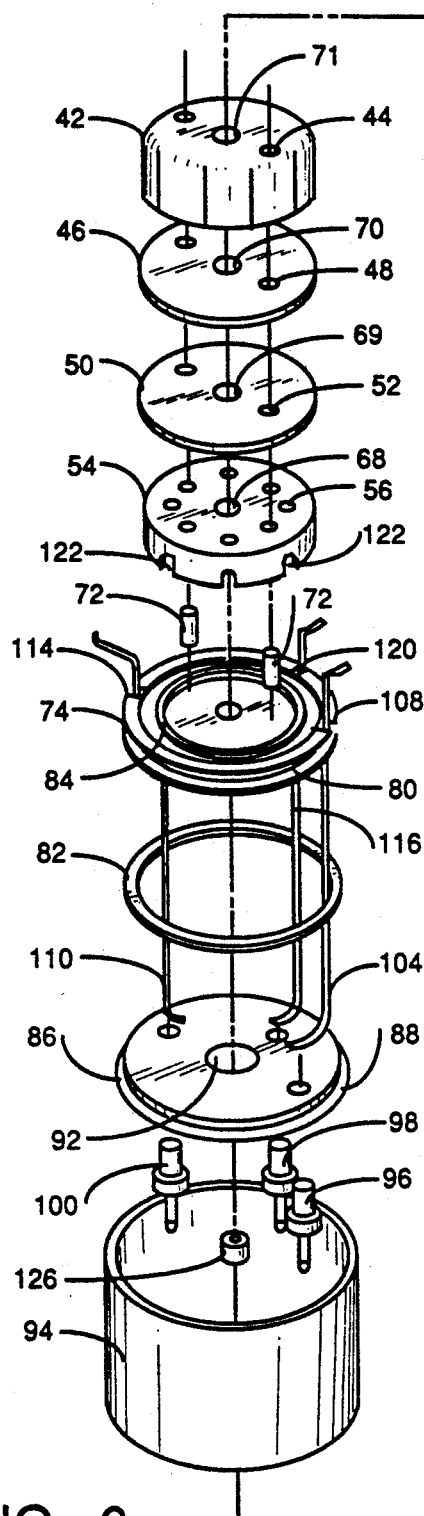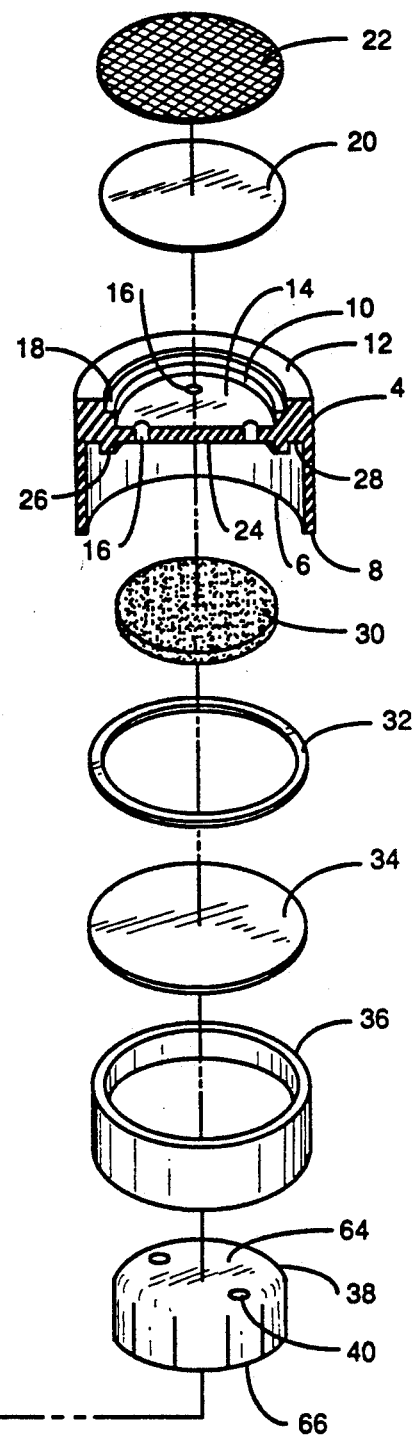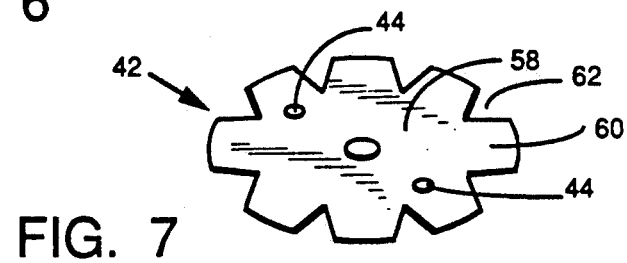
FIG. 6
FIG. 7

ELECTROCHEMICAL GAS SENSOR WITH WRAPAROUND REFERENCE ELECTRODE

BACKGROUND OF THE INVENTION

1. Field Of The Invention

This invention relates to electrochemical gas detectors and, more particularly, to a three-electrode electrochemical sensor having a compact design.

2. Background Art

The theory and general operation of three-electrode electrochemical sensors used in toxic or other gas detector systems are well known. These sensors, also referred to as cells, typically include a sensing electrode, a reference electrode spaced from the sensing electrode by a porous separating mat containing an aqueous-based electrolyte contacting the sensing and reference electrodes through the mat, and a counter electrode also separated from the reference electrode by a porous mat containing the electrolyte, and a gas diffusion limiting means. The sensing electrode can be a porous, gas diffusion electrode having a coating of a catalytic material on the surface adjacent to the electrolyte. The gas to be sensed, referred to as the object gas, diffuses either alone or in combination with other gases through the diffusion limiting means to the sensing electrode. The object gas undergoes a reaction, either a reduction or an oxidation, at the interface of the electrolyte and the catalytic material on the sensing electrode. The catalytic material is selected to promote the reaction with a particular object gas, but to catalyze little or none of the other gases that may accompany the object gas.

The reference electrode is used in conjunction with an electronic circuit to maintain a predetermined potential difference between the sensing and reference electrodes. This potential difference also is selected so as to encourage the desired oxidation or reduction reaction of the object gas at the sensing electrode. This potential difference also is selected so that other undesirable reactions will be suppressed as much as possible and, thereby, will not interfere with the desired reaction resulting from the presence of the object gas. The predetermined potential difference between the reference electrode and the sensing electrode is maintained by the electronic circuit without drawing current from the reference electrode. Within limits, this potential difference does not affect the magnitude of the current generated by the reaction of the object gas at the sensing electrode. The magnitude of the current is controlled by the diffusion limiting means.

The result of either the oxidation or reduction reaction at the sensing electrode is the production of ions and electrons. These charged ions migrate through the electrolyte to the counter electrode. A conductive wire or other conduction path is connected external of the cell between the sensing and counter electrodes to complete the electrical path, to allow electrons to flow between the counter and sensing electrodes, and to permit another electrochemical reaction to take place at the counter electrode. With all other conditions remaining constant, such as temperature, gas pressure, and humidity, the number of electrons generated by the reaction at the sensing electrode will be directly proportional to the amount of object gas diffusing to the sensing electrode. The electronic current flowing through the external circuit between the sensing and counter electrodes can be measured by an ammeter or the like and provide a quantitative reading of the concentration of object gas present.

Prior art three-electrode electrochemical sensors useful for detecting an object gas in an atmosphere are shown, for example, in U.S. Pat. Nos. Re. 31,914, Re. 31,915 and Re. 31,916. A two-electrode sensor is shown in U.S. Pat. No. 3,755,125. However, these sensors are rather bulky due to the positioning of the electrodes with respect to each other and because they require an electrolyte reservoir in the cell.

It is, accordingly, a first object of the present invention to provide a three-electrode electrochemical sensor for gas detection which has a compact design.

The prior art has provided numerous designs of three-electrode electrochemical sensors of compact design, as shown, for example, in U.S. Pat. Nos. 4,406,770, 4,521,290, 4,633,704 and 4,769,122, and U.K. Patent Application No. 2 140 566. See also U.S. Pat. Nos. 3,950,980, 4,025,412, 4,132,616, and 4,587,003.

The reference electrodes used in three-electrode electrochemical sensors are conveniently of the air type. While the steady-state air-electrode potential depends on variables such as gas pressure, temperature, and electrolyte composition, it is desirable that the reference potential be stable. However, fluctuations from this potential do occur in normal operation. Such fluctuations affect the accuracy of the measurements developed by a sensor, render the sensor less immune to interference from other gases, and cause the sensor's operation to vary over its life. This deviation in the air reference electrode's redox potential from the theoretical value is often characterized as an instability in the reference electrode potential. The stability problems with air reference electrodes are reduced or minimized in three-electrode electrochemical sensors when the overall air reference electrode is large in size. Problems have been observed when the reference electrode is reduced to the small sizes used in compact designs. In such compact electrochemical sensors, the reference electrode is often not sufficiently stable and reproducible to provide accurate, dependable and consistent gas measurements.

Therefore, it is a second object of the present invention to provide a compact, three-electrode electrochemical sensor for gas detection which includes a large and stable air reference electrode that can operate reliably at the air-electrode potential.

SUMMARY OF THE INVENTION

Therefore, we have developed an electrochemical sensor for gas detection which includes an impervious, nonconductive sensor body having a first cavity extending therein from a first end. The first cavity includes a plurality of sensor elements stacked therein including a sensing electrode positioned at an inner end of the first cavity and against the sensor body, a first mat positioned against the sensing electrode, a reference electrode positioned against the first mat, a second mat positioned against the reference electrode, and a counter electrode positioned against the second mat. The sensor also includes a support means positioned within the first cavity and holding the electrodes and mats in contact with each other and at the inner end of the first cavity. The sensor also includes means for making electrical contact with the electrodes therein. A cap means covers an open end of the first cavity and holds the support means therein. The support means and cap means define an electrolyte chamber therebetween which is at least partially filled with a liquid electrolyte. The sensor has a gas passage means through the body, such as a gas diffusion limiter formed of at least one capillary passage, for permitting gas to reach the sensing electrode. Means are provided for directing the liquid electrolyte to the mats and electrodes. The reference electrode has a central portion positioned between the sensing and counter electrodes and at least one extension attached thereto at an outer edge of the central portion and extending around the counter electrode and into contact with the liquid electrolyte.

In a preferred embodiment, the reference electrode has a plurality of projections attached thereto. In addition, the first mat preferably has a central portion disposed between the reference and sensing electrodes and a plurality of projections attached thereto along an outer edge of its central portion and extending completely thereabout. The first mat projections extend beyond and contact the reference electrode projections and also extend into contact with the liquid electrolyte. It is advantageous to form the reference electrode and first mat with a circular central portion and from an initially flat member which is formed into a cup-like structure when positioned within the first cavity.

A scrubber can be positioned between the sensing electrode and the gas passage means for removing one or more interfering gases from the gas to the sensor.

The support means is preferably a cup-shaped plunger positioned in the first cavity and having a closed end oriented toward the stacked electrodes and mats, and having an open end oriented toward the cap means. The extensions of the reference electrode and first mat extend around the plunger and between the plunger and the sensor body. The closed end of the plunger, as well as the counter electrode, second mat, reference electrode and first mat, can have at least one set of aligned holes therethrough for carrying liquid electrolyte to the electrodes and the mats. In addition, a liquid drawing wick can be positioned through at least one of the sets of aligned holes and extend into the electrolyte chamber.

The support means can also include a hollow, cylindrical ring positioned in the first cavity, surrounding the plunger, and contacting the sensing electrode. The extensions of the reference electrode and the first mat extend between the plunger and the cylindrical ring. The plunger can include a plurality of openings near its open end for carrying the liquid electrolyte to the extensions of the reference electrode and first mat.

The cap means can include an end plate positioned within the first cavity and contacting the open end of the plunger, and an end cover contacting the end plate and covering the open end of the first cavity. A vent plug can be provided in the end cap, with the vent plug including a gas porous but liquid impervious membrane which allows gases to pass therethrough and become dissolved in the liquid electrolyte.

BRIEF DESCRIPTION OF THE DRAWINGS

FIG. 1 is a front view of an electrochemical gas detecting sensor in accordance with the present invention;

FIG. 2 is a back view of the electrochemical sensor shown in FIG. 1;

FIG. 3 is a right side view of the electrochemical sensor shown in FIG. 2;

FIG. 6 is an exploded view, partially in section, of the electrochemical sensor shown in FIGS. 1-5; and FIG. 7 is a perspective view of a reference electrode, in a flat configuration, used in the electrochemical sensor shown in FIGS. 1-6.

DETAILED DESCRIPTION OF THE PREFERRED EMBODIMENT

Figure 4:
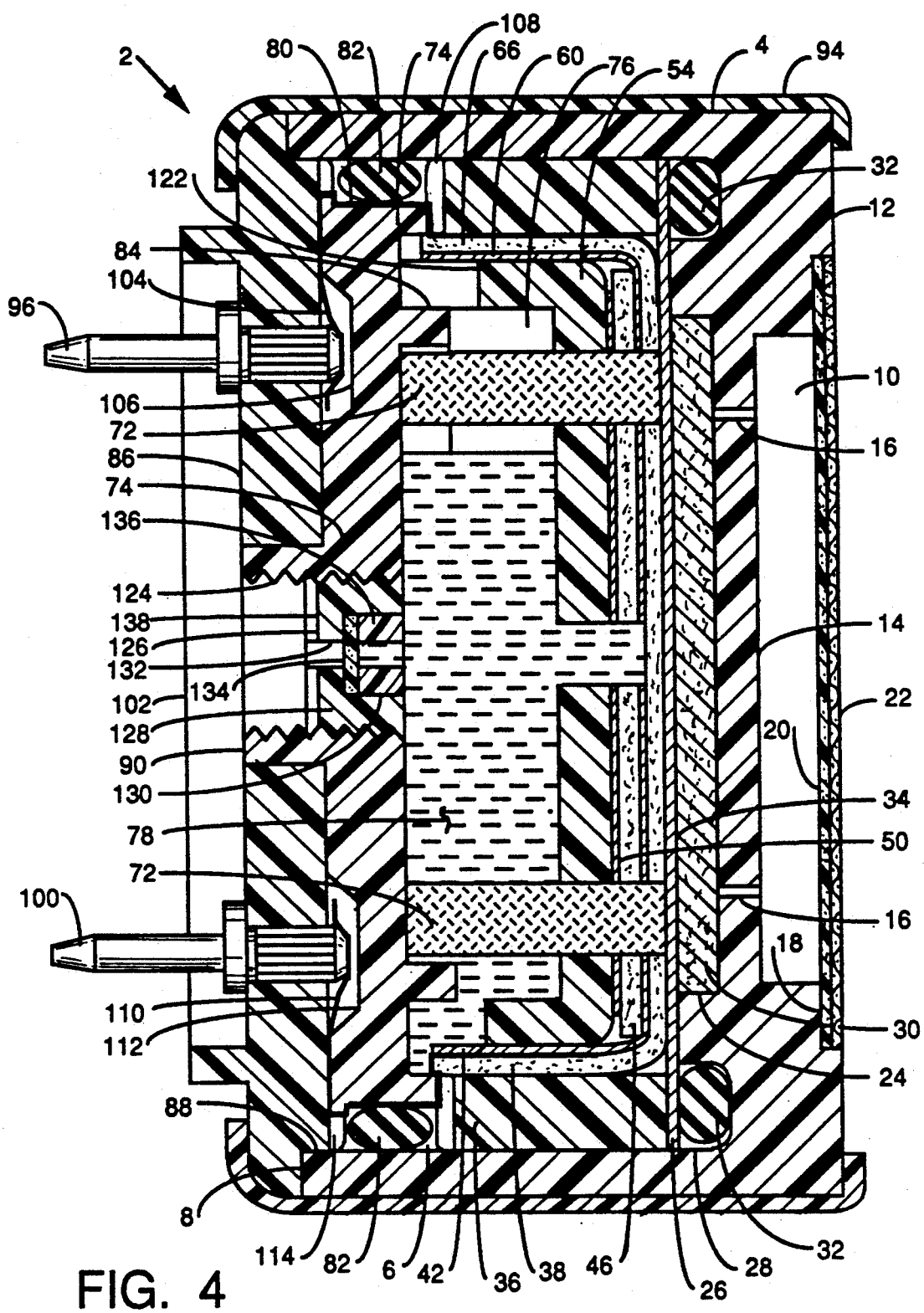
FIG. 4 is a section taken along lines IV—IV in FIG. 2.

Referring to FIGS. 1-6, there is shown an embodiment of a three-electrode, compact electrochemical sensor 2 for toxic or other gas detection in accordance with the present invention. The sensor 2 includes a cylindrically-shaped housing or body 4 which is formed of a relatively inert, nonconductive, gas impervious and acid resistant material, such as high density polyethylene, polypropylene or polyvinylchloride (PVC). A first or rear cavity 6, preferably cylindrical in shape, extends into the body 4 from a first or rear surface 8 thereof. A second or front cavity 10, also preferably cylindrical in shape, extends into the body 4 from a second or front surface 12 thereof. The rear cavity 6 has a depth substantially greater than that of the front cavity 10 because, as will be explained hereinafter in detail, the rear cavity 6 includes substantially all of the working elements of the electrochemical sensor 2 of the present invention. The rear cavity 6 and front cavity 10 are positioned in the approximate center of the rear surface 8 and front surface 12, respectively, of the body 4 and the central axis of each is aligned with the central axis of the body 4. The diameter of the front cavity 10 is somewhat smaller than the diameter of the rear cavity 6.

The rear cavity 6 and the front cavity 10 extend toward, but do not contact, each other and are separated by a dividing wall 14 in the body 4. The dividing wall 14 is preferably integral with and formed of the same material as the body 4. The dividing wall 14 has a plurality of capillaries 16 extending therethrough from the front cavity 10 to the rear cavity 6 and forming a gas diffusion limiter in the dividing wall 14. In a preferred embodiment, the dividing wall 14 of the sensor 2 includes four spaced apart and parallel capillaries 16, each having a length of about 1 mm and a diameter of about 0.25 mm. In order to keep the sensor 2 as small and compact as possible, a plurality of shorter capillaries 16 is preferred over a single, longer capillary, although each arrangement would function as a similar gas diffusion limiter.

A thin shoulder 18 is formed in the front surface 12 of the body 4 and surrounding the front cavity 10. A thin, circular porous disk 20 is positioned within the shoulder 18 and closing the front cavity 10. Additionally, a thin, circular screen 22 is positioned within the shoulder 18 above the porous disk 20. Shoulder 18 preferably has sufficient depth such that the porous disk 20 and screen 22 can be carried therein, yet provide a flush surface along the front surface 12 of the body 4 and the outer surface of the screen 22. A space is formed between the inner surface of the porous disk 20 and the outer surface of the dividing wall 14, which therebetween define the remaining area of the front cavity 10. The screen 22 functions to protect the fragile, porous disk 20. The porous disk 20 and the space between the porous disk 20 and dividing wall 14 function to reduce the effects of pressure fluctuations and of turbulence in the object gas before it reaches the gas diffusion limiter formed by the capillaries 16 and also prevents particulate contamination of the capillaries 16.

A recess 24 is formed in the body 4 at an inner end of the rear cavity 6 adjacent the dividing wall 14. This recess 24 is substantially cylindrical in shape and has an inner diameter smaller than the inner diameter of the rear cavity 6 and about equal to the inner diameter of the front cavity 10. Recess 24 defines shoulder 26 in the body 4 at the inner end of the rear cavity 6. Shoulder 26 also includes a circular, recessed groove 28 therein extending substantially about the inner diameter of the rear cavity 6. A scrubber or filter 30 is positioned within recess 24, in contact with the dividing wall 14 and adjacent the capillaries 16. An inner O-ring 32, formed of rubber or other resilient material, is positioned within groove 28.

A thin, planar, circular sensing electrode 34 is positioned at the inner end of the rear cavity 6 and in contact with the inner O-ring 32, shoulder 26, and filter 30. The sensing electrode 34 is held in place by a hollow, cylindrical ring 36 positioned within the rear cavity 6, and having its outer surface adjacent the body 4 and having its lower surface contacting the sensing electrode 34. A cup-shaped first mat 38 is positioned within the rear cavity 6 and within the ring 36, and is adjacent both the sensing electrode 34 and the inner surface of the ring 36. The first mat 38 includes a pair of holes 40 therethrough and separated by about 180°. A cup-shaped reference electrode 42 is positioned within the rear cavity 6 and within the ring 36, and is in contact with the first mat 38. The reference electrode 42 has a pair of holes therethrough, separated by about 180° and aligned with holes 40 in the first mat 38. A thin, planar, circular second mat 46 is positioned within the rear cavity 6 and within and adjacent the reference electrode 42. The second mat 46 has a pair of holes 48 therethrough, separated by about 180° and aligned with holes 44 in the reference electrode 42. A thin, planar, circular counter electrode 50 is positioned within the rear cavity 6 and adjacent the second mat 46. The counter electrode 50 includes a pair of holes 52 therethrough, separated by about 180° and aligned with holes 48 in the second mat 46. A cup-shaped plunger 54 is positioned within the rear cavity 6 and the ring 36, and has its outer or side surface contacting the first mat 38 and its inner or closed end contacting the counter electrode 50. The plunger 54 includes a plurality of holes 56 through its closed end, with two of holes 56 separated by about 180° and aligned with holes 52 on the counter electrode 50.

The sensing electrode 34, reference electrode 42 and counter electrode 50 are each preferably of the gas diffusion type. Any of the known gas diffusion electrodes which have been used in electrochemical gas sensors can be used in the present invention. In general, the electrodes include a porous catalytic material on a porous, conductive or insulating substrate. In a preferred embodiment, each of the electrodes 34, 42 and 50 are formed from a porous, hydrophobic Teflon ® substrate coated or impregnated with platinum black as the catalytic material.

In a preferred embodiment, the reference electrode 42 and first mat 38 are each initially formed as a flat member, but are formed into cup-like structures when they are positioned within the rear cavity 6. Such a reference electrode 42 is shown in its initial, flat configuration in FIG. 7. The reference electrode 42 includes a thin, planar, circular central portion 58 and a plurality of planar, rectangular projections 60 attached thereto and extending substantially completely about an outer edge of the central portion 58. The arrangement shown in FIG. 7 has notches 62 between the projections 60, but these notches 62 are eliminated when the flat member is formed into a cup-like structure and adjacent projections 60 contact each other along their respective edges. While the reference electrode 42 could be formed initially as a solid, cup-shaped structure, the arrangement shown in FIG. 7 and discussed above is much easier to manufacture. As shown in FIG. 6, the first mat 38 similarly includes a thin, planar, circular central portion 64 and a plurality of planar, rectangular projections 66 attached thereto and extending substantially completely about an outer edge of the central portion 64.

Referring again to FIGS. 1-6, the plunger 54 serves as a support means for holding the stacked electrodes 34, 42 and 50 and mats 38 and 46 within the rear cavity 6 and positioned at its inner end. The sensing electrode 34, the second mat 46 and the counter electrode 50, as well as the central portions 58 and 64, respectively, of the reference electrode 42 and first mat 38, and also the filter 30, are sandwiched between the closed end of the plunger 54 and the sensor body 4 at the inner end of the rear cavity 6 and at the dividing wall 14. The projections 60 and 66 of the reference electrode 42 and first mat 38, respectively, are sandwiched between the outer side surface of the plunger 54 and the inner surface of the ring 36. A central hole 68 extends through the inner, closed end of the plunger 54 and is aligned with central holes 69, 70 and 71 in the counter electrode 50, second mat 46 and reference electrode 42, respectively. Separate wicks 72 extend through two of holes 56 in the plunger 54 and also through holes 52, 48, 44 and 40 in the counter electrode 50, second mat 46, reference electrode 42 and first mat 38, respectively. The wicks 72 are used, as will be described hereinafter, for electrolyte communication between the various mats, but also help to align the various stacked elements of the sensor 2 which are positioned within the rear cavity 6.

A cylindrical end plate 74 is positioned within the rear cavity 6, near its open end, and adjacent and contacting the ring 36, the plunger 54 and the wicks 72. The end plate 74 functions to close off the rear cavity 6, near its open end, and to form an electrolyte chamber 76 in the remaining area of the rear cavity 6 between the interior area of the plunger 54 and an inner face of the end plate 74. The electrolyte chamber 76 is at least partially filled with a liquid electrolyte 78. The outer circumferential surface of the end plate 74 includes a recessed groove 80 therein which carries an outer O-ring 82. The outer O-ring 82, which is made of rubber or other resilient material, provides a liquid tight seal between the end plate 74 and the sensor body 4 and keeps the liquid electrolyte 78 from leaking out of the sensor 2. The end plate 74 includes an upstanding cylindrical lip 84 on its inner surface thereof. The outer, side surface of cylindrical lip 84 contacts the inner surface of the plunger 54 at its open end and firmly holds the plunger 54 and end plate 74 in contact with each other.

The open end of the rear cavity 6 is closed off and all of the elements positioned therein are held in place by a cylindrical end cover 86. The end cover 86 has a right angle offset 88 along its inner surface and along its outer circumference which mates with the rear surface 8 of the sensor body 4 to provide an area for adhesive, such as epoxy, between the end cover 86 and the sensor body 4. The end cover 86 and end plate 74 can be sealed together with epoxy or the like to form a single structure which is inserted over the rear cavity 6. The outer surface of the end plate 74 includes an upstanding cylindrical projection 90 in the center thereof which extends through a central hole 92 through the end cover 86. The end cover 86 or the end cover 86/end plate 74 structures can be affixed to the sensor body 4 by any known means, such as a metal sleeve 94 covering the sensor body 4 and extending over a portion of the end cover 86 and a portion of the front surface 12. The use of a metal sleeve 94 surrounding the sensor body 4 also functions to shield the sensor 2 from radio frequency interference.

The end cover 86 carries contact pins corresponding in number to the electrodes contained in the sensor 2. As shown in the drawings, the end cover 86 carries a sensing electrode contact pin 96, a counter electrode contact pin 98, and a reference electrode contact pin 100. These contact pins are formed of metal or other conductive material and have an inner portion extending through the end cover 86 and into a corresponding recess on the outer surface of the end plate 74. The contact pins also include an elongated outer portion extending outwardly beyond the outer surface of the end cover 86. These contact pins can be protected by a surrounding cylindrical lip 102 on the outer surface of the end cover 86. Electrical contact is made between the contact pins and the associated electrode by means of conductive electric ribbons which extend from the inner end of the contact pins adjacent the end plate 74 and the respective electrode. In addition, the outer circumferential surface of the end plate 74 includes slots through the recessed groove 80 to facilitate passage of the electrical ribbons around the end plate 74 and behind the outer O-ring 82 without requiring that the ribbons contact the sensor body 4.

Figure 5:
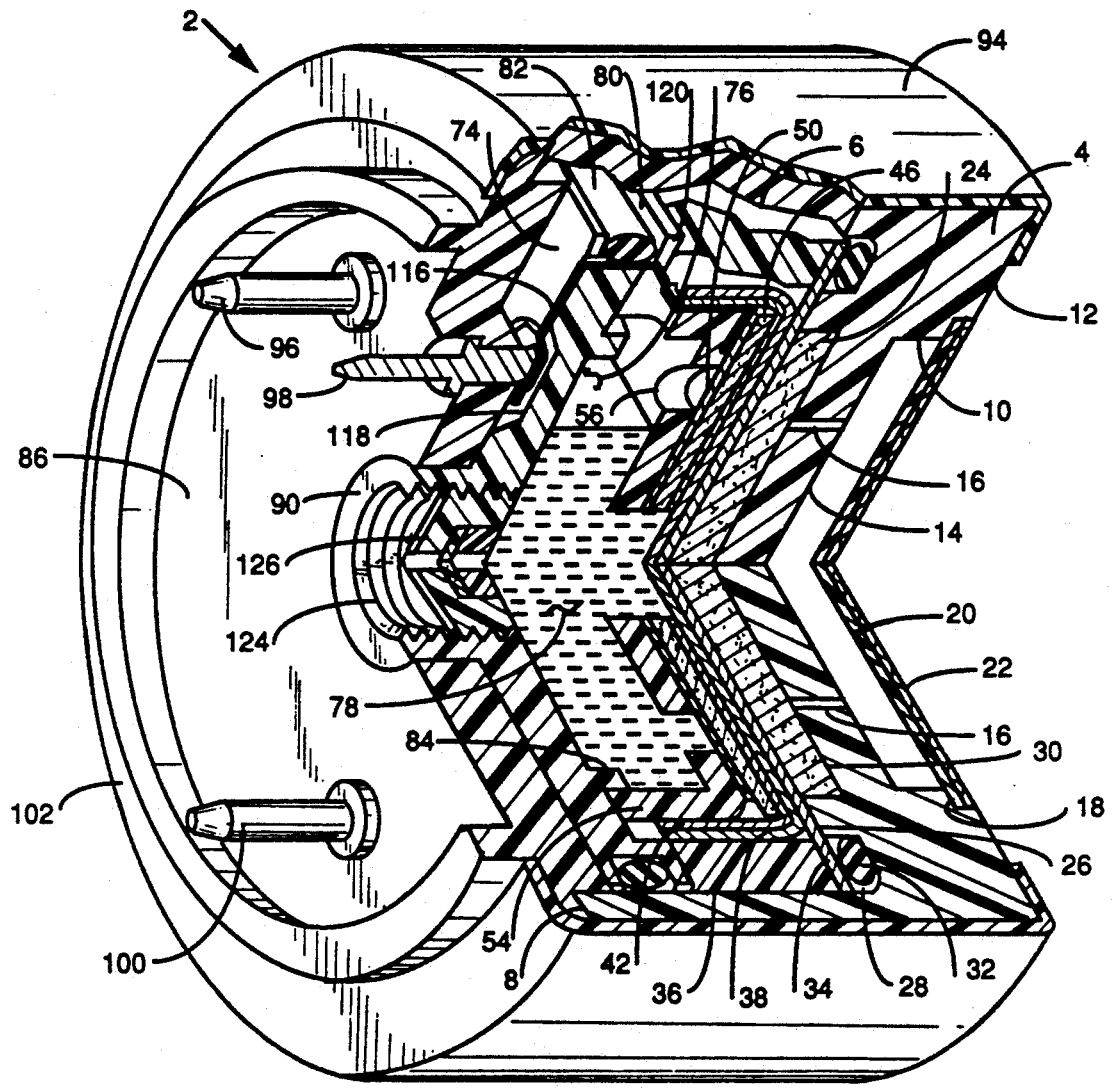
FIG. 5 is a section taken along lines V—V in FIG. 2.

In particular, and as shown in FIG. 4, a sensing ribbon 104 for the sensing electrode 34 extends from the inner end of the sensing electrode contact pin 96 within recess 106 on the end plate 74, between the end cover 86 and end plate 74, through a sensing ribbon slot 108 in the end plate 74 and behind the outer O-ring 82, between the projections 66 of the first mat 38 and the ring 36, and to the inner surface of the sensing electrode 34. A reference electrode ribbon 110 extends from the inner end of the reference electrode contact pin 100 within recess 112 on the end plate 74, between the end cover 86 and the end plate 74, through a reference ribbon slot 114 in the end plate 74 and behind the outer O-ring 82, between the projections 60 and 66 of the reference electrode 42 and first mat 38 where the reference electrode ribbon 110 contacts the reference electrode 42. Finally, as shown in FIG. 5, a counter electrode ribbon 116 extends from the inner end of the counter electrode contact pin 98 within recess 118 on the end plate 74, between the end cover 86 and the end plate 74, through a counter ribbon slot 120 in the end plate 74 and behind the outer O-ring 82, and between the outer surface of the plunger 54 and the reference electrode 42 to the counter electrode 50. In order to keep the counter electrode ribbon 116 from making electrical contact with the reference electrode 42, the rear surface of the reference electrode 42 is nonconducting.

The reference electrode 42 in this invention is a wraparound electrode; that is, the reference electrode 42 is provided with a plurality of integral projections 60 which extend around the counter electrode 50 and the plunger 54, between the plunger 54 and the ring 36 within the rear cavity 6, and into the electrolyte chamber 76. The first mat 38 is also formed in a wraparound arrangement similar in shape and configuration to the reference electrode 42. In this manner, the surface area of the reference electrode 42 is greatly expanded, increasing its electrochemical stability or its ability to operate stably at the practical air-oxygen redox potential, while maintaining an overall compact design for the sensor 2.

A plurality of notches 122 are formed through the plunger 54 near its open end and provide direct fluid communication of the liquid electrolyte 78 to the reference electrode 42 and first mat 38. The electrolyte 78 is drawn to the first mat 38 and second mat 46 along the wicks 72 extending from the electrolyte chamber 76, through the plunger 54 and ending in contact with the sensing electrode 34. Electrolyte 78 is also drawn through the central hole 68 to the electrodes and mats. A standard, acidic electrolyte, such as sulfuric acid, can be used in the sensor 2.

The first mat 38, the second mat 46, and the wicks 72 are each made of felt or a glass fiber filter type of material, such as fiberglass, which is capable of wicking a liquid from one location to another and holding the liquid therein. In this manner, the electrolyte 78 is drawn from the electrolyte chamber 76 and into contact with the sensing, reference and counter electrodes in contact with the respective mats or wicks. The plunger 54, ring 36, end plate 74 and end cover 86 are preferably made from the same material as the sensor body 4.

The operating oxygen/air for the reference electrode 42 may come from the gas which diffuses through the sensing electrode 34 and becomes dissolved in the electrolyte 78. However, it is advantageous to provide a direct path for oxygen diffusion to the reference electrode 42 within the sensor. In the embodiment shown in the figures, a threaded hole 124 extends axially through the end plate 74 and through the raised cylindrical projection 90. A vent plug 126 is threaded into this hole 124. The vent plug 126 includes a cylindrically-shaped body 128 having threads on its outer surface which match the threaded hole 124 in the end plate 74. A cylindrical vent cavity 130 extends into the vent plug body 128 from an inner surface thereof. A smaller vent passage 132 extends into the vent plug body 128 from an outer surface thereof and is connected to the inner end of the vent cavity 130 therein. A thin, gas permeable, but liquid impervious membrane 134 is positioned at the inner end of the vent cavity 130 adjacent the vent passage 132. The membrane 134 is secured in place by a hollow, cylindrical retaining ring 136 positioned within the vent cavity 130 and adjacent the membrane 134. A slot 138 can be provided along the outer surface of the vent plug 126 to allow the same to be threaded into and out of the threaded hole 124 in the end plate 74. In this manner, oxygen can diffuse through the membrane 134 and the rear cavity 6 and become dissolved in the liquid electrolyte 78, thus providing operating oxygen for the reference electrode 42.

The stacked arrangement of the counter electrode 50, reference electrode 42 and sensing electrode 34 operates in substantially the same manner as in prior art three-electrode electrochemical sensors. The sample gas, containing the object gas, passes through the protective screen 22 and the porous disk 20 and into the front cavity 10 above the dividing wall 14. The sample gas then passes through the diffusion limiter formed by capillaries 16 and to the electrodes in the rear cavity 6. Other gas passage arrangements for permitting the sample gas to reach the sensing electrode 34 can be used. Before reaching the sensing electrode 34, the gas may pass through an optional filter 30 or scrubber to remove other gases, such as potentially interfering gases, before reaching the sensing electrode 34. In one embodiment, the filter 30 is a porous alumina structure, formed as a small tablet or monolithic structure and impregnated with potassium permanganate ($KMnO_4$). Potassium permanganate is a strong oxidant and functions to remove $SO_2$ in a gas stream. The filter 30 may also be formed of multiple, stacked wafers.

The object gas is detected by the sensor 2 in the normal manner and generates an appropriate electrical signal. Electrical contact is made from the interior of the sensor 2 through the electric ribbons and to the appropriate external contact pins as described above. The sensor 2 shown herein can be connected to any of the known measuring and operating circuits through the contact pins.

EXAMPLE I

A carbon monoxide electrochemical gas sensor in accordance with the present invention was built and tested. The housing was machined from GE Noryl polymeric material. Four diffusion limiting capillaries were each nominally 0.05" long and had a diameter of 0.0093". The sensing electrode was a gas diffusion electrode made by spreading a mixture of high surface-area platinum-black and 10% Teflon ®-30 (Dupont) onto a porous Teflon ® sheet 0.005" thick (Norton Zitex), followed by pressing and sintering of the electrode. The reference and counter electrodes were made by the same procedure. The raw electrodes were cut into the shapes shown in FIGS. 6 and 7. The Teflon ®-30 particles improved the physical stability of the electrodes and created hydrophobic gas channels in the electrode structure permitting gases to diffuse to the three-phase-interphase of catalyst, electrolyte, and gas, where carbon monoxide is oxidized on the sensing electrode. The fiberglass mats holding the electrolyte were cut from Whatman 934-AH filter paper and were 0.015" thick. After assembling the components into the sensor as shown in FIG. 4, the fiberglass mats were flooded with sulfuric acid electrolyte.

The sensor was tested using a potentiostatic circuit with a 10 ohm load resistor. The sensing electrode potential was the same as that of the air-reference electrode. The output signal of this sensor was 32 nA per ppm carbon monoxide. The output signal was linear between 0 and 1000 ppm carbon monoxide.

EXAMPLE II

A sensor as described in Example I above was assembled, except that the diffusion limiting means in this sensor consisted of 12 capillaries of nominally 0.0093" diameter and 0.05" in length. When tested with 505 ppm carbon monoxide, this sensor's output was 76.2 nA per ppm. When tested with 100 ppm hydrogen sulfide, the output was 222 nA per ppm hydrogen sulfide. Subsequently, a filter designed to remove hydrogen sulfide from the gas stream was installed into the sensor; this filter did not affect the sensitivity to carbon monoxide, which now was 77.6 nA per ppm. However, the sensitivity to hydrogen sulfide was almost completely suppressed. The sensitivity to hydrogen sulfide was now 6.5 nA per ppm hydrogen sulfide.

Having described herein the presently preferred embodiment of the present invention, it is to be understood that the invention may be otherwise embodied within the scope of the appended claims.

We claim:

1. An electrochemical sensor for gas detection comprising an impervious, nonconductive sensor body having a first cavity extending therein from a first end thereof, said first cavity having a plurality of sensor elements stacked therein including a sensing electrode positioned at an inner end of said first cavity and against said sensor body, a first mat positioned against said sensing electrode, a reference electrode positioned against said first mat, a second mat positioned against said reference electrode, and a counter electrode positioned against said second mat, said sensor also including a support means within said first cavity for holding said electrodes and mats in contact with each other and at the inner end of said first cavity, contact means for making electrical contact with said sensing, counter and reference electrodes, cap means for covering an open end of said first cavity and holding said support means therein, said support means and cap means defining an electrolyte chamber therebetween, with said electrolyte chamber being at least partially filled with a liquid electrolyte, said sensor having gas passage means through said body for permitting gas to reach said sensing electrode, and electrolyte flow means for directing said liquid electrolyte to said mats and electrodes, with said reference electrode having a central portion disposed between said sensing and counter electrodes and having at least one extension attached thereto at an outer edge of said central portion and extending around said counter electrode and said support means and into contact with the electrolyte in said electrolyte chamber.

2. The electrochemical sensor of claim 1 wherein said first mat has a central portion disposed between said reference and sensing electrodes and at least one projection attached thereto at an outer edge of said central portion, with said first mat projection contacting the reference electrode projection and extending into contact with the electrolyte in said electrolyte chamber.

3. The electrochemical sensor of claim 1 wherein said reference electrode has a plurality of said projections attached thereto and extending around the outer edge of said central portion.

4. The electrochemical sensor of claim 3 wherein said first mat has a central portion disposed between said reference and sensing electrodes and a plurality of projections attached thereto along an outer edge of said central portion and extending around said control portion, with said first mat projections contacting the reference electrode projections and extending into contact with the electrolyte in said electrolyte chamber.

5. The electrochemical sensor of claim 4 wherein the central portion of said reference electrode and first mat are circular in shape and wherein said reference electrode and first mat are initially formed as a flat member but each form a cup structure when positioned within said first cavity.

6. The electrochemical sensor of claim 1 wherein said gas passage means is a diffusion limiter.

7. The electrochemical sensor of claim 6 wherein said diffusion limiter includes at least one capillary passage.

8. The electrochemical sensor of claim 1 further including a scrubber positioned between said sensing electrode and said gas passage means, with said scrubber removing one or more interfering gases from said gas flows.

9. The electrochemical sensor of claim 1 wherein said support means is a cup-shaped plunger positioned in said first cavity and having a closed end oriented toward said stacked electrodes and mats, and having an open end oriented toward said cap means, with the extensions of said reference electrode extending around said plunger and between said plunger and said sensor body.

10. The electrochemical sensor of claim 9 further including at least one set of aligned holes through, respectively, the closed end of said plunger, the counter electrode, the second mat, the reference electrode and the first mat for carrying the liquid electrolyte and air through said aligned holes and in contact with the electrodes and the mats.

11. The electrochemical sensor of claim 10 further including a liquid drawing wick extending from said electrolyte chamber and through at least one of said set of aligned holes.

12. The electrochemical sensor of claim 9 wherein said support means further includes a hollow, cylindrical ring positioned in said first cavity, surrounding said plunger and contacting said sensing electrode, with the planar extensions of said reference electrode extending between said plunger and said cylindrical ring.

13. The electrochemical sensor of claim 9 wherein said plunger includes a plurality of openings near its open end for carrying the liquid electrolyte and air to the extensions of said reference electrode.

14. The electrochemical sensor of claim 9 wherein said cap means includes an end plate positioned within said first cavity and contacting the open end of the plunger, and an end cover contacting said end plate and covering the open end of said first cavity.

15. The electrochemical sensor of claim 9 further including a vent plug in said end cap, with said vent plug including therein a gas porous but liquid impervious membrane which allows gases to pass therethrough and become dissolved in the liquid electrolyte.

16. An electrochemical sensor for gas detection comprising an impervious, nonconductive sensor body having a first cavity extending therein from a first end thereof, said first cavity having a plurality of sensor elements stacked therein including a sensing electrode positioned at an inner end of said first cavity and against said sensor body, a first mat positioned against said sensing electrode, a reference electrode positioned against said first mat, a second mat positioned against said reference electrode, and a counter electrode positioned against said second mat, said sensor including a cup-shaped plunger within said first cavity for holding said electrodes and mats in contact with each other and at the inner end of said first cavity, said sensor also including a contact means for making electrical contact with said sensing, counter and reference electrodes, cap means for covering an open end of said first cavity and holding said support means therein, with said plunger having a closed end oriented toward the stacked electrodes and mats and having an open end oriented toward said cap means, said plunger and cap means defining an electrolyte chamber therebetween, with said electrolyte chamber being at least partially filled with a liquid electrolyte, said sensor having gas passage means through said body for permitting gas to reach said sensing electrode, and electrolyte flow means for directing said liquid electrolyte to said mats and electrodes, with said reference electrode having a central portion disposed between said sensing and counter electrodes and having at least one extension attached thereto at an outer edge of said central portion and extending around said counter electrode and said plunger and into contact with the electrolyte in said electrolyte chamber, and with said first mat having a central portion disposed between said reference and sensing electrodes and at least one projection attached thereto at an outer edge of said central portion, with said first mat projection extending about and contacting the reference electrode projection and extending into contact with the electrolyte in said electrolyte chamber.

17. The electrochemical sensor of claim 16 further including a hollow, cylindrical ring positioned in said first cavity, surrounding said plunger and contacting said sensing electrode, with the extensions of said reference electrode and said first mat extending between said plunger and said cylindrical ring.

18. An electrochemical sensor for gas detection comprising an impervious, nonconductive sensor body having a first cavity extending therein from a first end thereof, said first cavity having a plurality of sensor elements stacked therein including a sensing electrode positioned at an inner end of said first cavity and against said sensor body, a first mat positioned against said sensing electrode, a reference electrode positioned against said first mat, a second mat positioned against said reference electrode, and a counter electrode positioned against said second mat, said sensor including a cup-shaped plunger within said first cavity for holding said electrodes and mats in contact with each other and at the inner end of said first cavity, said sensor also including a contact means for making electrical contact with said sensing, counter and reference electrodes, cap means for covering an open end of said first cavity and holding said support means therein, with said plunger having a closed end oriented toward the stacked electrodes and mats and having an open end oriented toward said cap means, said plunger and cap means defining an electrolyte chamber therebetween, with said electrolyte chamber being at least partially filled with a liquid electrolyte, said sensor having gas passage means through said body for permitting gas to reach said sensing electrode, and electrolyte flow means for directing said liquid electrolyte to said mats and electrodes, with said reference electrode having a central portion disposed between said sensing and counter electrodes and having a plurality of extensions attached thereto at an outer edge of said central portion and extending around said counter electrode and said plunger and into contact with the electrolyte in said electrolyte chamber.

19. The electrochemical sensor of claim 18 wherein said first mat has a central portion disposed between said reference and sensing electrodes and a plurality of projections attached thereto along an outer edge of said central portion and extending around said central portion, with said first mat projections contacting the reference electrode projections and extending into contact with the electrolyte in said electrolyte chamber.

20. The electrochemical sensor of claim 18 further including a hollow, cylindrical ring positioned in said first cavity, surrounding said plunger and contacting said sensing electrode, with the extensions of said reference electrode and said first mat extending between said plunger and said cylindrical ring.

* * * * *

UNITED STATES PATENT AND TRADEMARK OFFICE
CERTIFICATE OF CORRECTION

PATENT NO. : 5,284,566
DATED : February 8, 1994
INVENTOR(S) : Carlo E. Cuomo, Alfred Kutschker, Peter M. Noble and Robert L. Novack It is certified that error appears in the above-indentified patent and that said Letters Patent is hereby corrected as shown below:

Claim 4 Line 47 Column 10 "control" should read --central--.

Signed and Sealed this

Fourteenth Day of June, 1994

Attest:

BRUCE LEHMAN

Attesting Officer   Commissioner of Patents and Trademarks